(12) United States Patent
Rusnak et al.

(10) Patent No.: US 10,821,270 B2
(45) Date of Patent: Nov. 3, 2020

(54) DIALYSIS CATHETER

(71) Applicants: Joseph G. Rusnak, East Aurora, NY (US); Raymond Zygaj, West Seneca, NY (US); John Fitzgerald, Orchard Park, NY (US)

(72) Inventors: Joseph G. Rusnak, East Aurora, NY (US); Raymond Zygaj, West Seneca, NY (US); John Fitzgerald, Orchard Park, NY (US)

( * ) Notice: Subject to any disclaimer, the term of this patent is extended or adjusted under 35 U.S.C. 154(b) by 595 days.

(21) Appl. No.: 14/959,835

(22) Filed: Dec. 4, 2015

(65) Prior Publication Data

US 2017/0157367 A1     Jun. 8, 2017

(51) Int. Cl.
| | | |
|---|---|---|
| A61M 25/10 | (2013.01) | |
| A61M 25/00 | (2006.01) | |
| A61M 1/36 | (2006.01) | |
| A61M 25/01 | (2006.01) | |

(52) U.S. Cl.
CPC .......... *A61M 25/10* (2013.01); *A61M 1/3661* (2014.02); *A61M 25/003* (2013.01); *A61M 25/0102* (2013.01); *A61M 2025/0019* (2013.01); *A61M 2025/0031* (2013.01); *A61M 2025/1068* (2013.01)

(58) Field of Classification Search
CPC .. A61M 25/10; A61M 25/003; A61M 1/3661; A61M 2025/0019; A61M 2025/0031; A61M 2025/702
USPC .......................................................... 604/267
See application file for complete search history.

(56) References Cited

U.S. PATENT DOCUMENTS

| | | | | |
|---|---|---|---|---|
| 5,141,499 | A * | 8/1992 | Zappacosta | A61M 1/285 604/175 |
| 5,336,178 | A * | 8/1994 | Kaplan | A61B 8/12 604/103.01 |
| 5,395,316 | A * | 3/1995 | Martin | A61M 25/0028 604/284 |
| 8,246,568 | B2 * | 8/2012 | Hardert | A61M 25/0068 604/508 |
| 9,067,063 | B2 * | 6/2015 | Chi Sing | A61N 5/1001 |
| 2001/0001113 | A1 * | 5/2001 | Lim | A61F 2/958 604/96.01 |
| 2003/0059370 | A1 * | 3/2003 | Quijano | A61K 47/6847 424/1.49 |

(Continued)

*Primary Examiner* — Nathan R Price
*Assistant Examiner* — John A Doubrava
(74) *Attorney, Agent, or Firm* — Hodgson Russ LLP (57) ABSTRACT

A dialysis catheter is provided. A first lumen extends through a first tubular member from a proximal portion to a distal portion, and a first orifice at the distal portion provides an opening through the first tubular member to the first lumen. The first tubular member further includes an inflation lumen extending longitudinally at least partially through a length of the first tubular member. A balloon is operably connected to an outer surface of the first tubular member proximal to the first opening, is in fluid communication with the inflation lumen. A second tubular member has a proximal portion connected to the outer surface of the first tubular member. A distal portion of the second tubular member is connected to the balloon wall. A second lumen extends through the second tubular member, and a second orifice provides an opening through the second tubular member at the distal portion.

12 Claims, 7 Drawing Sheets

(56) References Cited

U.S. PATENT DOCUMENTS

| | | | | |
|---|---|---|---|---|
| 2005/0245900 A1* | 11/2005 | Ash | ............... | A61M 25/0017 604/537 |
| 2008/0306427 A1* | 12/2008 | Bailey | ............... | A61M 25/10 604/6.16 |
| 2011/0166516 A1* | 7/2011 | Orr | ............... | A61M 25/10 604/103.01 |
| 2011/0245665 A1* | 10/2011 | Nentwick | ............... | A61M 1/285 600/433 |

* cited by examiner

DIALYSIS CATHETER

BACKGROUND OF THE DISCLOSURE

Dialysis catheters are used for varying durations in patients undergoing hemodialysis. Such catheters may be used for periods of time varying from days (or less) to an indefinite period of time—i.e., weeks, months, or longer. Such catheters are used to exchange blood to and from a hemodialysis machine when the patient is undergoing treatment. Once a treatment session is complete, the catheter is disconnected from the machine and left inserted in the patient until the next session.

Between treatment sessions, a patient's body may create clots or other thromboid obstructions at the catheter. Similarly, a fibrin sheath may form around the catheter lumens within the body. Such thrombus and fibrin sheaths create poor performance when a technician attempts to use the catheter during the next treatment. Blood flow through the catheter can be partially or completely restricted. Partially restricted flow causes extended treatment sessions which are problematic for the patient, who must sit through an long session, and the clinic, which must make available additional equipment and personnel to attend to the longer sessions. This results in additional costs to both the patient and the clinic.

If blood flow through the catheter is completely restricted or restricted to where use of the catheter is impractical, the catheter must be replaced. This requires the scheduling and use of a surgical facility and additional medical staff, including a surgeon, to replace the device. Furthermore, the surgery and the introduction of a new catheter brings a greater possibility of infection than the risk associated with continued use of an existing catheter.

For this reason, there is a long-felt need for a dialysis catheter which is usable despite obstructions and/or has allows a user to clear obstructions once they have formed.

BRIEF SUMMARY OF THE DISCLOSURE

The present disclosure may be embodied as a dialysis catheter. The catheter has a first tubular member with a proximal portion and a distal portion. A first lumen extends longitudinally through the first tubular member. A first orifice at the distal portion of the first tubular member provides an opening through the first tubular member to the first lumen. The first tubular member further includes an inflation lumen extending longitudinally at least partially through a length of the first tubular member. A balloon is operably connected to an outer surface of the first tubular member proximal to the first opening. The balloon has a balloon wall at least partially surrounding the first tubular member. The balloon is configured for disrupting occluding material when occluding material is present near the distal portion of the catheter. The inflation lumen is in fluid communication with the balloon such that the balloon may be selectively inflated or deflated by way of the inflation lumen. The catheter also has a second tubular member with a proximal portion connected to the outer surface of the first tubular member. A distal portion of the second tubular member is connected to the balloon wall. A second lumen extends through the second tubular member, and a second opening connects the second lumen at the distal portion of the second tubular member.

Embodiments of the presently disclosed device provide catheters which can clear obstructions such as, for example, thrombosis/fibrin, from the distal end in order to enhance blood flow into and/or out of the catheter. Using such a catheter also allows for cost savings because the ability to clear obstructions will reduce the need to replace obstructed catheters.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1A:
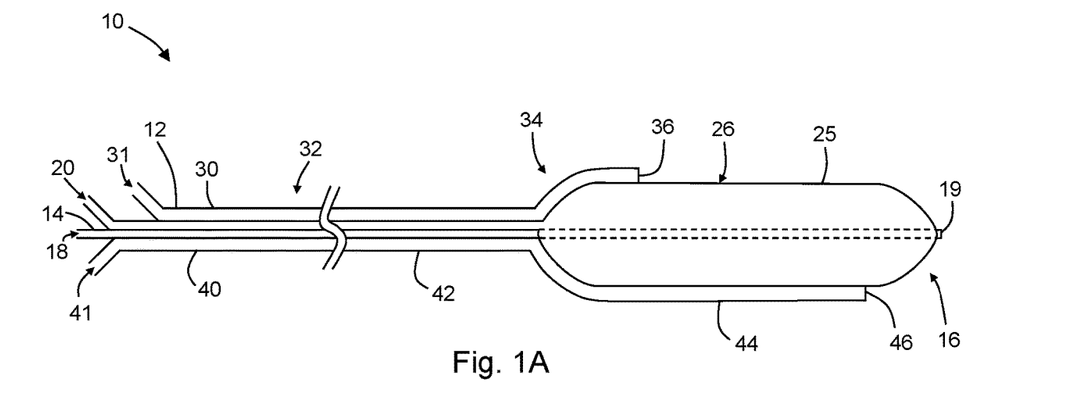
FIG. 1A depicts a dialysis catheter according to an embodiment of the present disclosure, wherein the balloon is shown inflated.
Figure 1B:
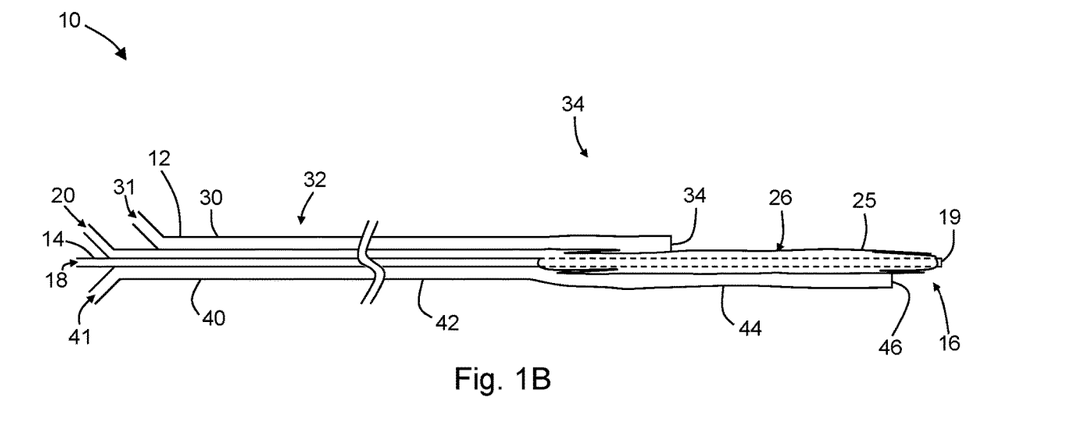
FIG. 1B depicts the dialysis catheter of FIG. 1A shown with the balloon deflated.
Figure 1C:
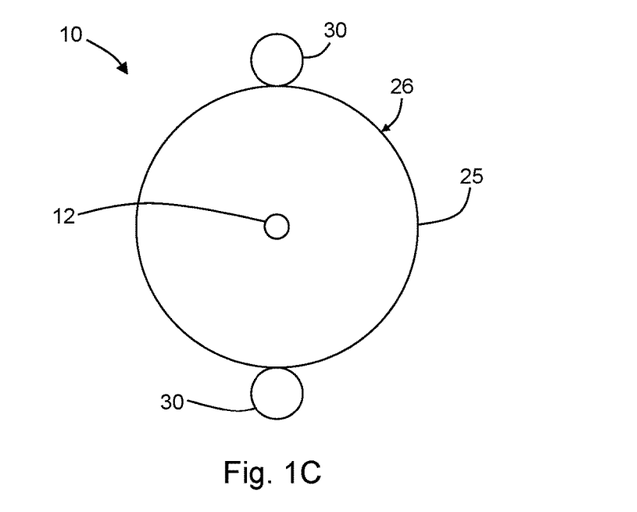
FIG. 1C is an end view of the dialysis catheter of FIGS. 1A and 1B.

With reference to FIGS. 1A-1C, the present disclosure can be embodied as a dialysis catheter 10. The catheter 10 has a first tubular member 12 with a proximal portion 14 and a distal portion 16. A first lumen 18 extends longitudinally through the first tubular member 12. A first orifice 19 at the distal portion 16 of the first tubular member 12 provides an opening through the first tubular member 12 to the first lumen 18. The first opening 19 is depicted at an end of the first tubular member 12, however it may be positioned in other locations on the tubular member 12 at the distal portion 16 (i.e., near the distal end). The first tubular member 12 further includes an inflation lumen 20 extending longitudinally at least partially through a length of the first tubular member 12.

The catheter 10 has a balloon 25 operably connected to an outer surface 13 of the first tubular member 12. The balloon 25 is positioned distally on the length of the first tubular member 12 and proximate the first opening 19. The balloon 25 has a balloon wall that surrounds or partially surrounds the first tubular member 12 along a portion of the length of the member 12. The inflation lumen 20 is in fluid communication with the balloon 25 such that the balloon 25 may be selectively inflated or deflated. In some embodiments, when inflated, the balloon 25 increases in a transverse diameter with respect to the longitudinal length of the first tubular member 12. When deflated, the balloon 25 is preferably configured to reduce in diameter such that a diameter of the catheter 10 at a position including the balloon 25 is not significantly greater than a diameter of the catheter 10 at a position which does not include the balloon 25. In this way, by inflating the balloon 25, occluding material, such as, for example, a fibrin sheath formed at the distal portion of the catheter 10 can be disrupted such that blood flow through the catheter 10 can be improved. The balloon 25 can be inflated in way known in the art, for example, the balloon 25 may be inflated by injecting saline into the balloon 25 by way of the inflation lumen 20.

The balloon 25 may be generally shaped as a sphere, or have a longer dimension such that the balloon 25 is more ovoid in shape. Other shapes for such balloons are known and within the scope of the present disclosure. The balloon 25 may be made of an elastomeric material such that the balloon wall is capable of stretching when the balloon 25 is inflated. In other embodiments, the balloon is made from a material that generally does not stretch when the balloon is inflated.

The catheter 10 includes a second tubular member 30 having a primary portion 32 connected to the outer surface 13 of the first tubular member 12 and a distal portion 34 connected to an outer surface 26 of the balloon wall. The second tubular member 30 has a second lumen 31 extending longitudinally therethrough. The distal portion 34 of the second tubular member 30 has a second opening 36 connected to the second lumen 31 (i.e., second orifice 36 at the distal portion 34 of the second tubular member 30 provides an opening through the second tubular member 30 to the second lumen 31.) The second lumen 31 is sized for use with dialysis. As such, the second lumen 31 should allow for a flow rate as high as 200 to 800 ml/min or more.

The catheter 10 may further comprise a third tubular member 40 having a primary portion 42 connected to the outer surface 13 of the first tubular member 12 and a distal portion 44 connected to an outer surface 26 of the balloon wall. The third tubular member 40 has a third lumen 41 extending longitudinally therethrough. The distal portion 44 of the third tubular member 40 has a third opening 46 connected to the third lumen 41. The third lumen 41 is sized for use with dialysis. As such, the third lumen 41 should allow for a flow rate as high as 200 to 800 ml/min or more. In some embodiments, the third tubular member 40 extends distally beyond the second tubular member 30. In such cases, the third opening 46 can be located at a longitudinal position which is further distal than the second opening 36.

Figure 6:
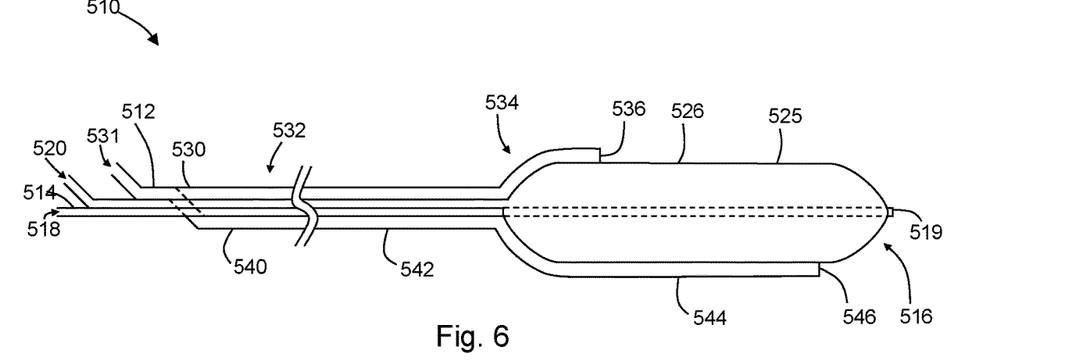
FIG. 6 depicts a dialysis catheter according to another embodiment of the present disclosure, wherein the balloon is shown inflated.

In some embodiments, such as the catheter 510 depicted in FIG. 6. The second tubular member 530 and the third tubular member 540 are connected such that such that the second lumen 531 is in fluid communication with the third lumen 541. In this way, the second and third lumen are accessible by way of a proximal port.

Figure 3A:
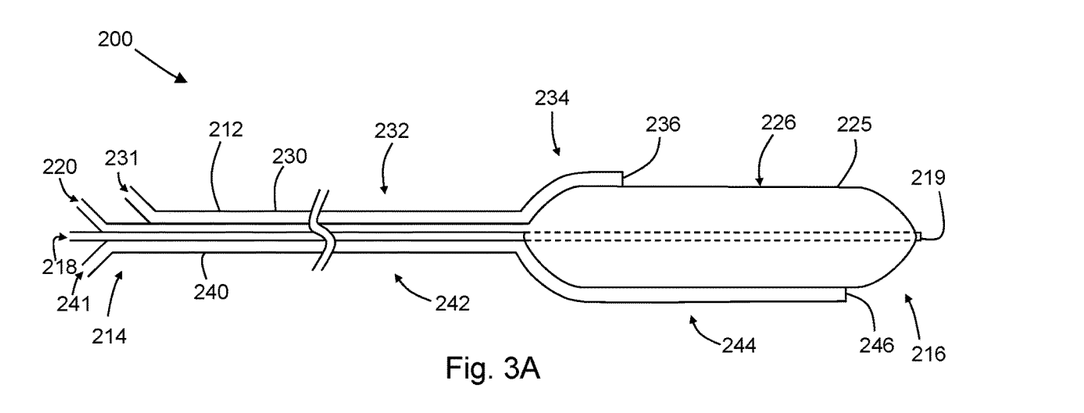
FIG. 3A depicts a dialysis catheter according to another embodiment of the present disclosure, wherein the balloon is shown inflated.
Figure 3B:
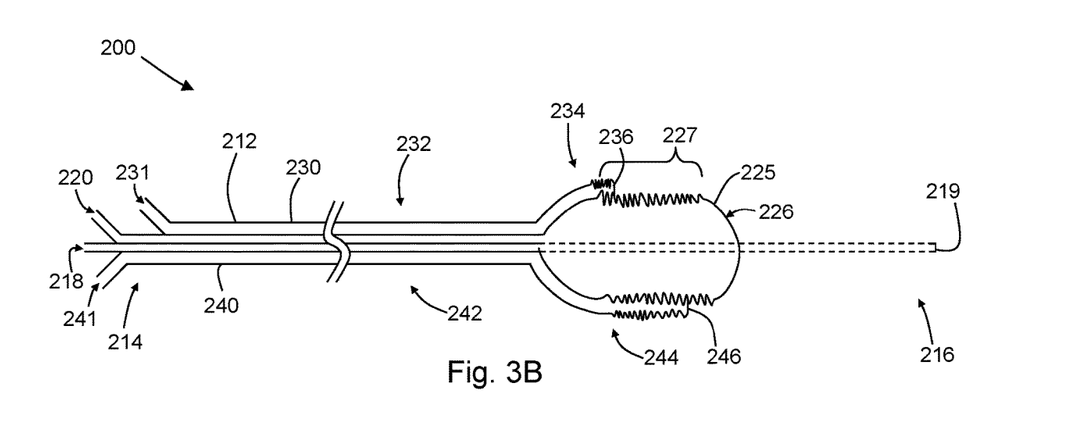
FIG. 3B depicts the dialysis catheter of FIG. 3A shown with the balloon partially deflated.

While generally, catheter balloons will expand and contract by changing diameter (i.e., changing size in the radial direction), in some embodiments of the present disclosure, a balloon 225 of a catheter 200 is configured to extend longitudinally when inflated and retract longitudinally when deflated. At least a portion of the balloon 225 may be a bellows, may have pleats, and/or may be otherwise configured to retract in a longitudinal direction.

Figure 4:
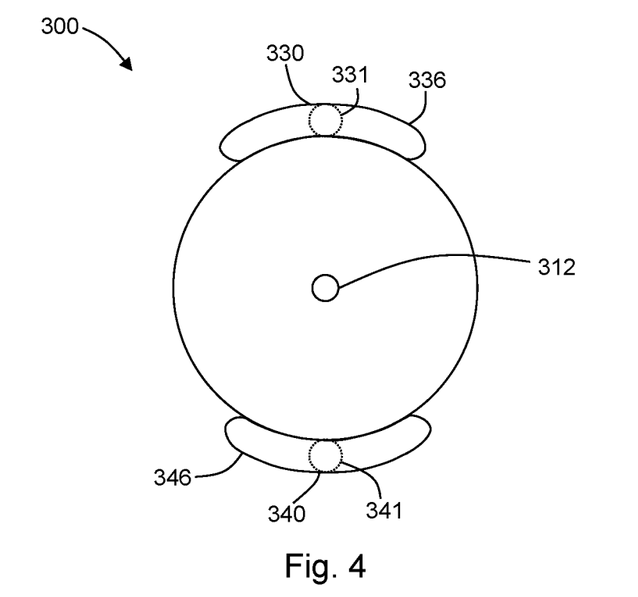
FIG. 4 is an end view of a dialysis catheter according to another embodiment of the present disclosure.

In some embodiments of catheters according to the present disclosure, the a tubular member may be flared such that a distal opening of the tubular member has a cross-sectional area which is greater than the cross-sectional area of the tubular member over a majority of its length. In this way, the proclivity of an opening to become obstructed by, for example, a thrombosis/fibrin, is reduced. For example, FIG. 4 shows a distal-end view of a catheter 300 having a first tubular lumen 312, a second tubular member 330, and a third tubular member 340. The ends of the second and third tubular lumens have been flared (i.e., the second opening 336 and the third opening 346 have been flared) such that the cross-sectional area at the opening is greater than the cross-sectional area of the corresponding lumen (shown in dotted lines). In particular, it can be seen in the figure that the second opening 336 has an area when viewed from an end (i.e., the cross-section area) that is greater than the cross-sectional area of the second lumen over a majority of its length (shown as dotted line 331). Similarly, third opening 346 is shown as having a cross-sectional area that is greater than the cross-sectional area of the third lumen (dotted line 341).

Figure 2A:
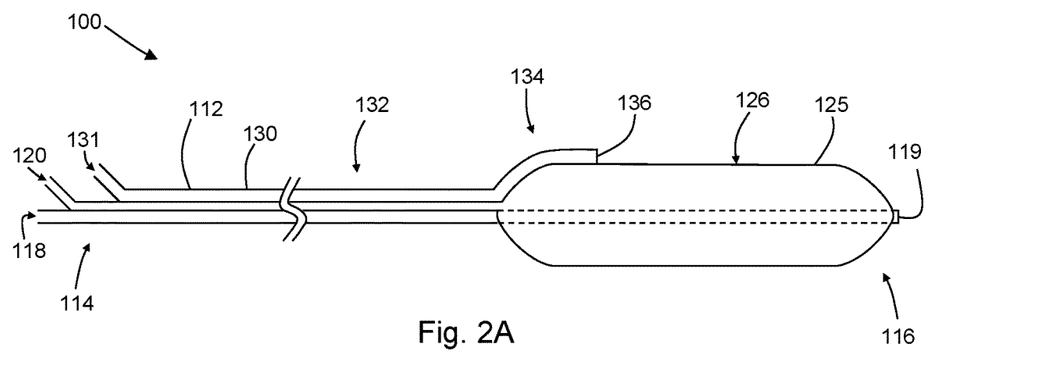
FIG. 2A depicts a dialysis catheter according to another embodiment of the present disclosure, wherein the balloon is shown inflated.
Figure 2B:
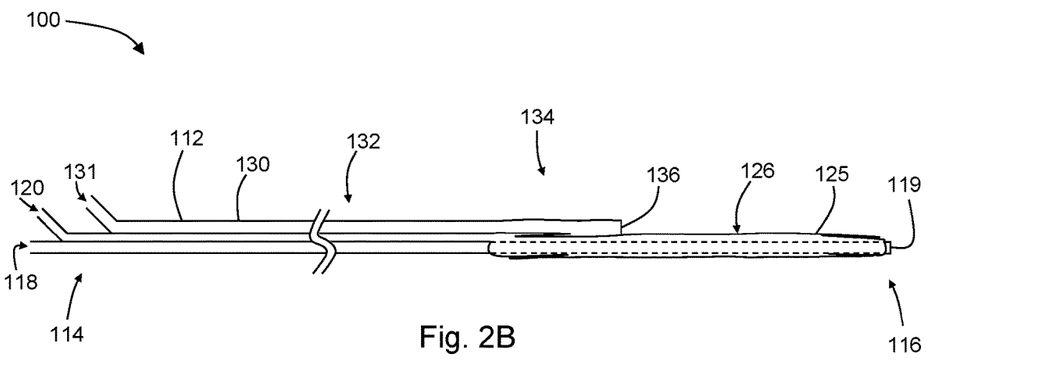
FIG. 2B depicts the dialysis catheter of FIG. 2A shown with the balloon deflated.
Figure 2C:
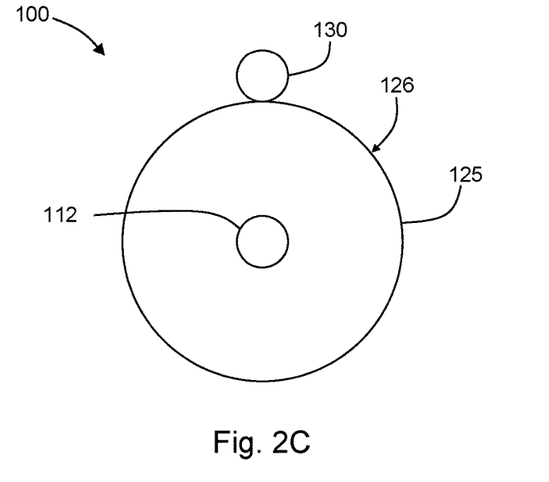
FIG. 2C is an end view of the dialysis catheter of FIGS. 2A and 2B.
Figure 5:
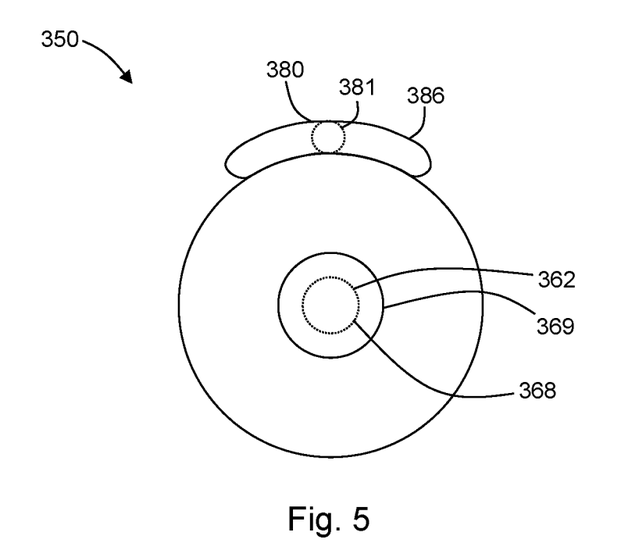
FIG. 5 is an end view of a dialysis catheter according to another embodiment of the present disclosure.

FIG. 5 shows a distal-end view of a catheter 350 having no third tubular member—similar to the catheter depicted in FIGS. 2A-2C. In catheter 350, it can be seen that the second tubular member 380 has an opening 386 which is flared to have a larger cross-sectional area than that of the second lumen 381. In this embodiment, it can also be seen that the first tubular member 362 has a flared opening (first opening 369) which has a larger cross-sectional area than that of the first lumen (dotted line 368).

Figure 7:
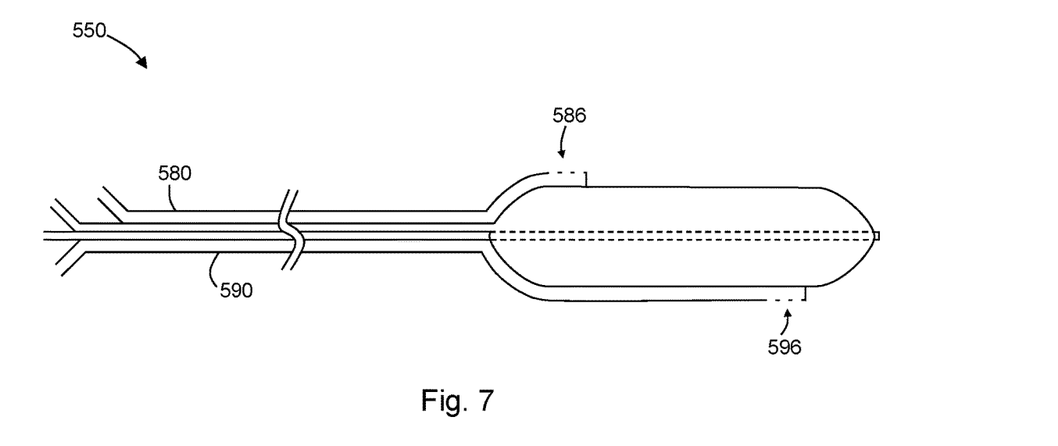
FIG. 7 depicts a dialysis catheter according to another embodiment of the present disclosure, wherein the balloon is shown inflated.

FIG. 7 depicts another embodiment of a catheter 550 wherein the tubular members include more than one opening. For example, it can be seen that the second tubular member 580 has a second opening 586 which comprises multiple openings. Similarly, the third tubular member 590 has third opening 596 which comprises multiple openings. It should be noted that the multiple openings need not be aligned on the respective tubular members and may be positioned at differing locations along the length and/or around the circumference of the tubular member.

Figure 8:
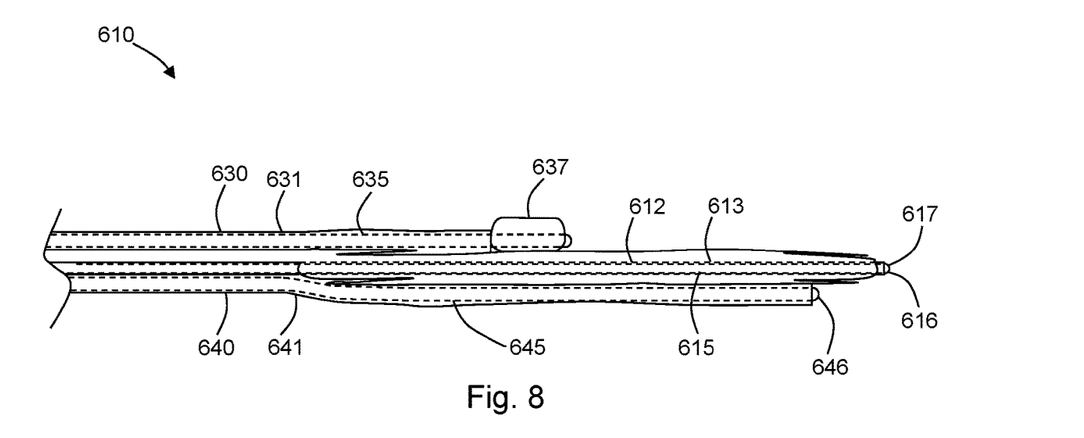
FIG. 8 depicts a dialysis catheter having stylets according to another embodiment of the present disclosure, wherein the balloon is shown deflated and a stylet balloon is shown inflated.

Catheters of the present disclosure may further comprise one or more stylets. Such stylets are configured to be disposed through a lumen of the catheter in order to occlude the lumen (and the corresponding opening) when the catheter is not in use. In this case, the term "in use" means that the catheter remains installed in an individual, but the catheter is not being used to transfer fluids. By disposing a stylet through the lumen, the stylet can be removed and the lumen and opening are unobstructed. FIG. 8 depicts a catheter 610 having a stylet disposed through each lumen (except for the inflation lumen). For example, the third tubular member 640 has lumen 641 through which third stylet 645 is disposed. In can be seen in the figure that the tip end 646 of the third stylet 645 emerges from the opening of the third lumen 641. Other configurations are comprehended within the present scope where the tip end of a stylet does not emerge through the corresponding opening, or, in other cases, extends for some distance beyond the corresponding opening.

Stylets may include additional features that enhance the function of a catheter. For example, first tubular member 612 has a first lumen 613 through which a stylet 615 is disposed. The tip end 616 of the stylet 615 can be configured to detect the presence of bacteria or other pathogens. For example, tip end 616 may include an indicator 617 configured to indicate the presence of bacteria. In this way, the stylet 615 may be used by a medical technician to quickly detect whether an infection has occurred. As such, the infection may be quickly addressed rather than waiting for more gross indications of infection, which may be at a time where the infection is more difficult to treat. The indicator 617 may be a reactive substance which changes color or fluoresces at the indicator location. In other embodiments, the indicator may be remote (e.g., at a proximal end of the stylet, outside of the patient's body) and may indicate that bacteria is detected at the distal end of the stylet.

In other stylets, a balloon is disposed at the distal end of the stylet so that obstructions may be cleared by inflating the stylet balloon. For example, in exemplary catheter 610 depicted in FIG. 8, the second tubular member 630 includes a second lumen 631 through which stylet 635 has been inserted. The stylet 635 comprises stylet balloon 637. In this case, stylet 635 may be hollow or may further comprise an inflation lumen such that stylet balloon 637 may be operably inflated. When catheter 610 is not in use, the stylet 635 may be inserted through the second lumen 631 and the stylet balloon 637 may remain deflated. When the catheter 610 is about to be used, the stylet balloon 637 can be inflated and deflated to break up any obstructions, such as, a thrombosis/fibrin, and then the stylet 635 can be removed from the second lumen 631. The stylet balloon 637 may remain within the second lumen 631 when deflated and then pushed beyond the opening of the second lumen 631 before inflation. In other embodiments, the stylet 635 may be configured to extend beyond the opening of the second lumen even when the stylet balloon 637 is deflated. Combinations of stylet features can be used. For example, a stylet can include both an indicator for infection and a stylet balloon.

Figure 9:
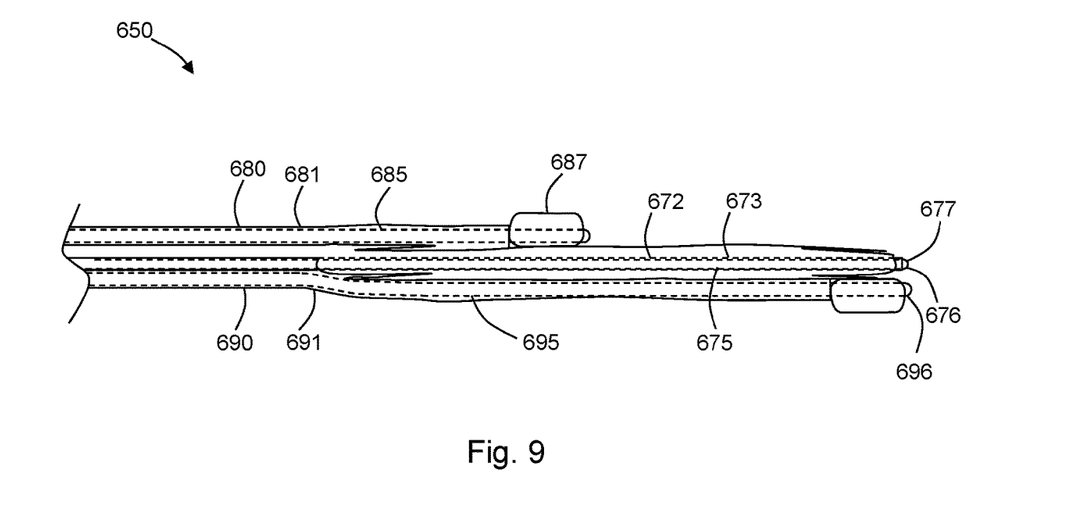
FIG. 9 depicts a dialysis catheter having stylets according to another embodiment of the present disclosure, wherein the balloon is shown deflated and two stylet balloons are shown inflated.

In another example depicted in FIG. 9, catheter 650, the second tubular member 680 includes a second lumen 681 through which stylet 685 has been inserted. The stylet 685 comprises stylet balloon 687. In this case, stylet 685 may be hollow (e.g., may further comprise an inflation lumen) such that stylet balloon 687 may be operably inflated. Similarly, stylet 695 is disposed through a third lumen 691. Stylet 695 includes a balloon 697. When catheter 650 is not in use, the stylets 685,695 may be inserted through their respective lumens 681,691 and the stylet balloons 687,697 may remain deflated. When the catheter 650 is about to be used, one or more of the stylet balloons 687,697 can be inflated and deflated to break up any obstructions, such as, a thrombosis/fibrin, and then the stylets 685,695.

Figure 10:
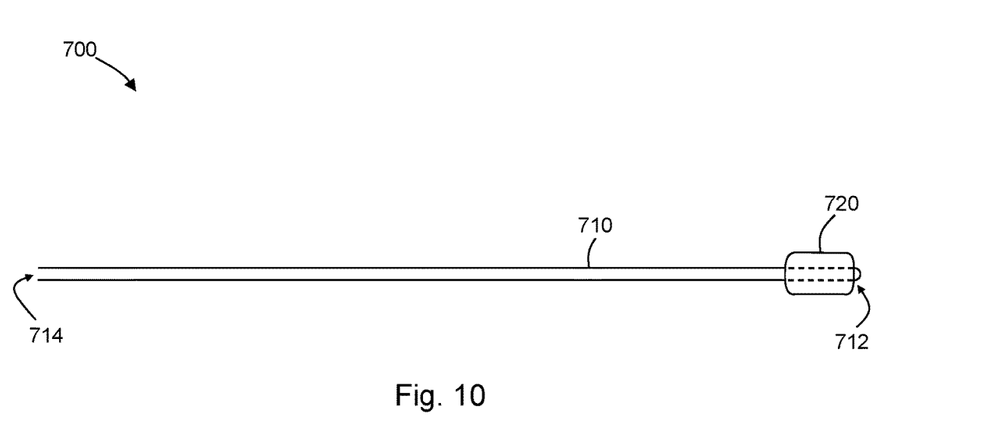
FIG. 10 depicts a balloon stylet according to another embodiment of the present disclosure.

In another aspect of the present disclosure, a balloon stylet 700 (see, e.g., FIG. 10) is provided. The balloon stylet 700 is configured for clearing obstructions from a catheter, for example, the stylet 700 may be configured to clear thrombosis/fibrin from the distal end of a catheter. The balloon stylet 700 includes a shaft 710 and a balloon 720 disposed on a distal end 712 of the shaft 710. The shaft has a lumen 714 from a proximal end to the distal end 712 and terminating at an orifice through the shaft 710 such that the balloon 720 may be inflated and deflated by way of the lumen 714. In some embodiments, the lumen 714 does not form a passageway throughout the entire longitudinal length of the shaft 710, but terminates at an orifice near the distal end 712 (e.g., short of the distal-most end of the shaft 710). The balloon stylet 700 can be made from any suitable materials known for such medical devices. In an embodiment, the balloon stylet 700 is made from a material which has a stiffness greater than the stiffness of a corresponding catheter for which it is designed.

Figure 11:
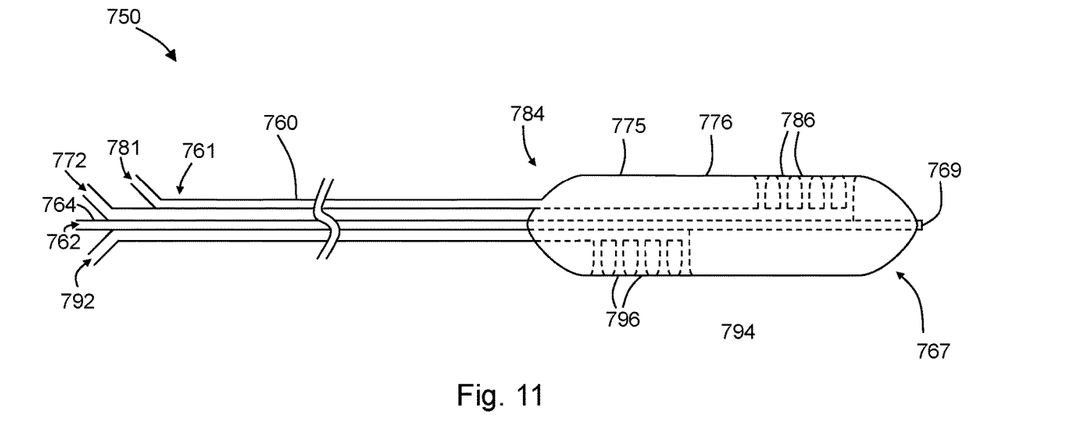
FIG. 11 depicts a dialysis catheter according to another embodiment of the present disclosure, wherein the balloon is shown inflated.

In another embodiment, a dialysis catheter 750 comprises a first tubular member 760 having a proximal portion 761, a distal portion 767 and a first lumen 762 extending longitudinally therethrough (see FIG. 11). The distal portion 767 includes a first opening 769 connected to the first lumen 762. The first tubular member 760 further includes an inflation lumen 781 extending at least partially through the first tubular member 760. The catheter 750 includes a balloon 775 operably connected to an outer surface of the first tubular member 760 proximal to the first opening 769. The balloon includes a balloon wall 776 at least partially surrounding the first tubular member 760 and configured to disrupt occluding material when occluding material is present near the distal portion 767 of the catheter 750. The inflation lumen 781 is in fluid communication with the balloon 775 for selective inflation and deflation of the balloon 775.

The first tubular member 760 includes a second lumen 772 extending therethrough. The distal portion 767 of the first tubular member 760 includes one or more second openings 786 connected to the second lumen 772 and disposed at least partially through the balloon 775. In this way, the second lumen 772 may be a part of the first tubular member 760 and located centrally with respect to the balloon 775. In similar fashion, a third lumen 792 may extend through the first tubular member 760, and the third lumen 792 may include one or more third openings 796 connecting the third lumen 792 through the balloon 775 to the exterior of the catheter 750.

Although the present disclosure has been described with respect to one or more particular embodiments, it will be understood that other embodiments of the present disclosure may be made without departing from the spirit and scope of the present disclosure. The following are non-limiting sample claims intended only to further illustrate exemplary embodiments.

The invention claimed is:

1. A dialysis catheter, the catheter comprising:
a first tubular member having a proximal portion, a distal portion, a first lumen extending longitudinally therethrough and an inflation lumen extending at least partially through the first tubular member, the distal portion comprising a first opening connected to the first lumen;
a balloon operably connected to an outer surface of the first tubular member proximal to the first opening, the balloon having a balloon wall at least partially surrounding the first tubular member and configured for disrupting occluding material when occluding material is present near the distal portion of the catheter, wherein the inflation lumen is in fluid communication with the balloon for selective inflation and deflation of the balloon;
a second tubular member having a proximal portion connected to the outer surface of the first tubular member and a distal portion connected to the balloon wall and configured such that the distal portion of the second tubular member is radially spaced apart from the first tubular member when the balloon is inflated, the second tubular member having a second lumen extending therethrough, the distal portion of the second tubular member having a second opening connected to the second lumen, wherein the second lumen is configured for a flow rate of at least 200 ml/min; and a third tubular member having a proximal portion connected to the outer surface of the first tubular member and a distal portion connected to the balloon wall and configured such that the third tubular member is circumferentially spaced apart from the second tubular member when the balloon is inflated, the third tubular member having a third lumen extending therethrough, the distal portion of the third tubular member having a third opening connected to the third lumen, wherein the third lumen is configured for a flow rate of at least 200 ml/min; and wherein the third tubular member extends distally beyond the second tubular member.

2. The catheter of claim 1, wherein the third opening is located at a longitudinal position which is further distal than the second opening.

3. The catheter of claim 1, wherein the second tubular member and the third tubular member are connected at the proximal end such that the second lumen is in fluid communication with the third lumen.

4. The catheter of claim 1, wherein the balloon is configured to extend longitudinally when inflated and to retract longitudinally when deflated.

5. The catheter of claim 1, wherein the balloon is made from an elastic material.

6. The catheter of claim 1, wherein a distal end of the second tubular member is flared such that the second opening has a cross-sectional area which is greater than a cross-sectional area of the second lumen over a majority of a length of the second lumen.

7. The catheter of claim 1, wherein the second opening comprises a plurality of openings.

8. The catheter of claim 1, further comprising a removable stylet configured to be inserted through the first lumen to occlude the first lumen and first opening when the catheter is not in use to transfer fluids.

9. The catheter of claim 4, wherein the balloon has a bellows portion.

10. The catheter of claim 8, wherein the stylet has a distal tip configured to detect the presence of a pathogen.

11. The catheter of claim 8, wherein the stylet includes a stylet balloon at a distal end, the stylet balloon configured for selective inflation and deflation.

12. The catheter of claim 10, wherein the stylet has an indicator in operable communication with the distal tip, and the indicator is configured to indicate when bacteria is detected by the distal tip.

* * * * *